United States Patent [19]
Kohayakawa

[11] Patent Number: 5,325,134
[45] Date of Patent: Jun. 28, 1994

[54] KERATOMETER

[75] Inventor: Yoshimi Kohayakawa, Yokohama, Japan

[73] Assignee: Canon Kabushiki Kaisha, Tokyo, Japan

[21] Appl. No.: 994,462

[22] Filed: Dec. 21, 1992

Related U.S. Application Data

[63] Continuation of Ser. No. 555,646, Jul. 23, 1990, abandoned.

[30] Foreign Application Priority Data

Jul. 28, 1989 [JP] Japan .................................. 1-197650

[51] Int. Cl.$^5$ ................................................ A61B 3/10
[52] U.S. Cl. ..................................... 351/212; 351/211; 351/221
[58] Field of Search ................ 351/211, 212, 221, 247

[56] References Cited

U.S. PATENT DOCUMENTS 4,572,628 2/1986 Nohda .................................. 351/212
4,597,648 7/1986 Feldon et al. ......................... 351/212

FOREIGN PATENT DOCUMENTS 1-19896 4/1989 Japan .

*Primary Examiner*—William L. Sikes
*Assistant Examiner*—Hung Xuan Dang
*Attorney, Agent, or Firm*—Fitzpatrick, Cella, Harper & Scinto

[57] ABSTRACT

A keratometer in which at least three point sources of light in an area exceeding a semicircular area are projected onto the cornea of an eye to be examined and the center of an ellipse is specified on the basis of the position information of all the three cornea-reflected images and the shape of an ellipse linking the positions of the reflected images when the point sources of light exist on the circumference of the same circle is found to thereby measure the shape of the cornea of the eye to be examined.

11 Claims, 2 Drawing Sheets

KERATOMETER

This application is a continuation of application Ser. No. 555,646, filed Jul. 23, 1990, now abandoned.

BACKGROUND OF THE INVENTION

1. Field of the Invention

This invention relates to a keratometer used in ophthalmic hospitals for measuring the shape of the cornea of an eye to be examined, 2. Related Background Art There is known a keratometer as disclosed in Japanese Patent Publication No 1-19896 wherein three point sources of light on the circumference of the same circle including two points in a diametrical direction are projected onto the cornea of an eye to be examined, the positions of the images reflected by the cornea are detected and the center of an ellipse is found from the intermediate position of the reflected images of the two points in the diametrical direction and further an ellipse linking the three reflected images is specified to thereby measure the shape of the cornea.

However, in the above-described example of the prior art, in the process of calculating the shape of the ellipse, the information of the positions of only two of the three reflected images is used to calculate the center of the ellipse linking the three reflected images and thus, although the information of the positions of the three reflected images is measured, all the information is not utilized and the accuracy of the measured value of the shape of the cornea is reduced.

Also, three point sources of light are provided on a plane perpendicular to the optic axis of the eye to be examined and on a half of the circumference of the circle centered at the optic axis and therefore, when these point sources of light are projected onto the cornea of the eye to be examined, the projected positions incline toward one side of the cornea and the point sources of light are not at all projected onto the other side of the cornea and thus, the measured value of the shape of the cornea does not at all contain the information of that half of the cornea. Since generally the cornea is asymmetrical, this measured value of the shape of the cornea which does not at all contain the information of that half of the cornea is low in reliability. To obtain the information of the remaining half of the cornea to thereby enhance the accuracy of measurement, a total of four or more point sources of light is necessary if further point sources of light are provided. Also, the point sources of light must be provided on a half of the circumference of a circle and therefore, their design positions are considerably limited and the degree of freedom in designing the apparatus is small.

SUMMARY OF THE INVENTION

It is an object of the present invention to enhance the accuracy of the measured value of the shape of an asymmetrical cornea on the basis of the entire information of the asymmetrical cornea by the use of at least three point sources of light.

It is also an object of the present invention to provide a keratometer in which the limitation in the positions at which these point sources of light are provided can be alleviated to thereby increase the degree of freedom in designing the apparatus.

DESCRIPTION OF THE PREFERRED EMBODIMENTS

Figure 1:
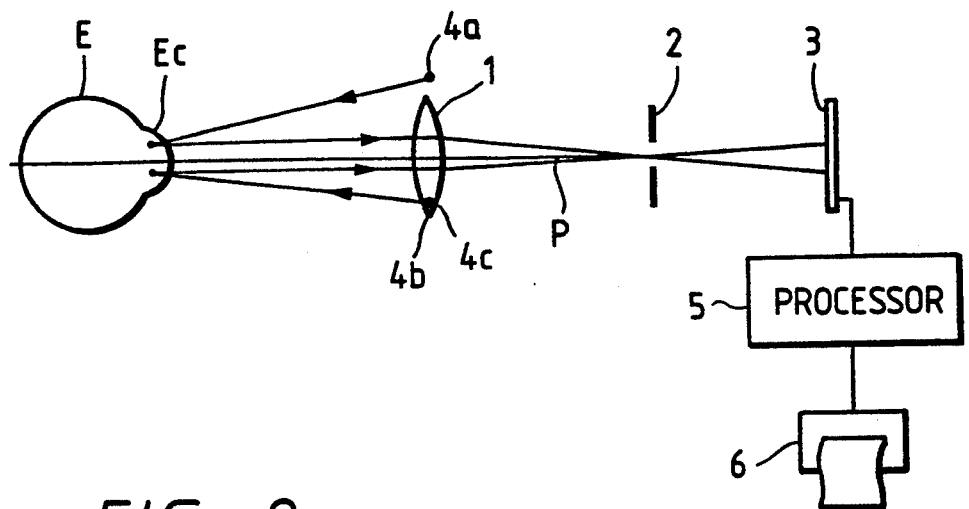
FIG. 1 shows the construction of a first embodiment of the present invention.
Figure 2:
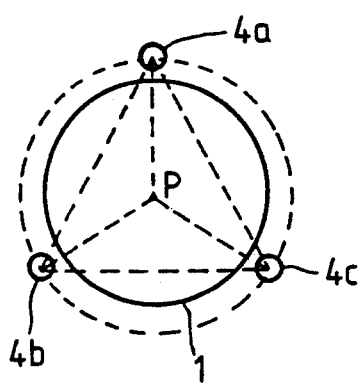
FIG. 2 shows the arrangement of measuring light sources according to the first embodiment.

Referring to FIG. 1 which shows the construction of an apparatus according to a first embodiment of the present invention, a stop 2 and an image sensor 3 are provided on the optic axis P rearward of an objective lens 1 opposed to an eye E to be examined, and further, as shown in FIG. 2, three light sources 4a–4c for measuring the shape of the cornea of the eye E to be examined are disposed near the objective lens 1 and in a plane perpendicular to the optic axis P at equal angles of 120° on the circumference of a circle about the optic axis P. The output of the image sensor 3 is connected to an output apparatus such as a printer 6 via a processor 5 which has a calculating unit in which the procedure of calculation to be described is programmed.

Light beams emitted from the light sources 4a–4c are reflected by the cornea Ec of the eye E to be examined, and project three reflected images 4A - 4C on the image sensor 3 via the objective lens 1 and the stop 2. Generally, the cornea Ec can be regarded as a rotation-elliptical surface containing astigmatism therein and therefore, the reflected images 4A - 4C formed by the light beams from the light sources 4a–4c disposed on the same circle about the optic axis P being reflected by the cornea Ec exist on a single ellipse about the optic axis P on the image sensor 3. The coordinate positions of the reflected images 4A - 4C and the optic axis P on the image sensor 3 are read by the processor 5, and this ellipse is found by calculation, and the degree of astigmatism, the angle of astigmatism and the radius of curvature are calculated from the ellipticity of the ellipse, the direction of the main meridian and the length of the main meridian, respectively, and are output to the printer 6.

Figure 3:
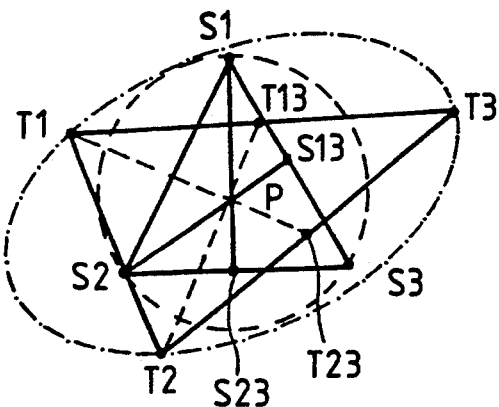
FIG. 3 illustrates a method of calculating the shape of a cornea according to the first embodiment.

Generally, ellipses passing through three points are numberless and therefore, unless the center of an ellipse is given, an ellipse cannot definitely be determined. Actually, the reflected images 4A - 4C can be observed on the image sensor 3, but the position of the optic axis P cannot be observed and therefore, it is necessary that the position of the optic axis P be first calculated from the positions of the reflected images 4A - 4C. The method of calculating the position of the optic axis P will now be described. FIG. 3 is an illustration in which the positions of the light sources 4a–4c, the reflected images 4A - 4C and the optic axis P are projected onto the same plane perpendicular to the optic axis P, and the positions of the light sources 4a–4c, the reflected images 4A - 4C and the optic axis P are designated by points S1, S2, S3, T1, T2, T3 and P, respectively. Apparently, the point P is the center of gravity of a triangle S1S2S3, and assuming that the midpoint between the points S1 and A2 is S13 and the midpoint between the points S2 and S3 is S23, the point of intersection between a segment S1S23 and a segment S2S13 coincides with the center of gravity P of the triangle S1S2S3. Assuming that the reflected image points at which the point S23 and the point S13 are to be reflected by the cornea Ec are T23 and T13, the image points T23 and T13 also are the midpoints of a segment T2T3 and a segment T1T3, respectively. Thus, the point of intersection between a segment T1T23 and a segment T2T13 coincides with the position of the optic axis P. Accordingly, an elliptical shape can be determined from the positions of the three points T1, T2 and T3 forming an ellipse and the optic axis P.

Figure 4:
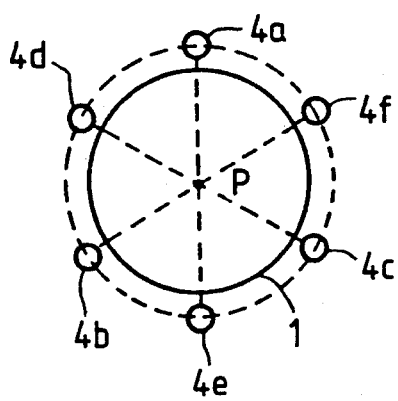
FIG. 4 shows the arrangement of measuring light sources according to a second embodiment.

In a second embodiment of the present invention, the construction of the apparatus is substantially similar to that of the first embodiment, but as shown in FIG. 4, in addition to the light sources 4a-4c provided in the first embodiment, three light sources 4d-4f are added so as to form an angle of 60° with respect to the light sources 4a-4c on the circumference of the same circle as the light sources 4a-4c. As in the first embodiment, light beams emitted from the light sources 4a-4c and the light sources 4d-4f form reflected images 4A - 4C and reflected images 4D - 4F on the image sensor 3. So, as in the first embodiment, discrete ellipses are determined from the positions of the reflected images 4A - 4C and the reflected images 4D - 4F by the previously described method, and then the shape of the cornea is calculated, and the average value of two elliptical shapes is used as the result of the measurement of the shape of the cornea. If in this case, the light emission time of the light sources 4a-4c and the light sources 4d-4f is divided, a distinction can be easily drawn between the two sets of reflected images 4A - 4C and 4D - 4F. Considering that the cornea Ec is a vertically asymmetrical rotation-elliptical surface, this can enhance the accuracy of measurement more than when as in the first embodiment, the shape of the cornea is calculated from only the positions of the three reflected images 4A - 4C.

Where as in the first and second embodiments, the light sources 4 are disposed at equal angles, the cornea-reflected images are projected onto the image sensor 3, but alternatively, a one-dimensional sensor may be used instead of the image sensor 3 and three reflected images may be projected onto the one-dimensional sensor, and the central position of the cornea Ec may be calculated from the position thereof to thereby accomplish the measurement of the shape of the cornea.

Figure 5:
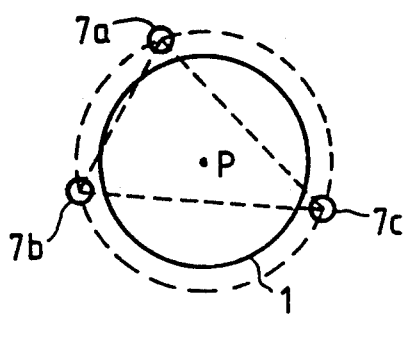
FIG. 5 shows the arrangement of measuring light sources according to a third embodiment.

FIG. 5 shows a third embodiment. In the third embodiment, the construction of the apparatus is substantially similar to that of the first embodiment, and three light sources 7a-7c for the measurement of the shape of the cornea are disposed on a plane perpendicular to the optic axis P near the objective lens 1 and at any angles with respect to one another on the circumference of a circle about the optic axis P. As in the first embodiment, light beams emitted from these light sources 7a-7c project three reflected images 7A - 7C onto the image sensor 3. Again in this embodiment, the light sources 7a-7c are provided on the circumference of the same circle and therefore, the reflected images 7A - 7C thereof also exist on a single ellipse about the optic axis P. However, as in the first embodiment, the ellipse cannot primarily be determined from only the positions of the three reflected images 7A - 7C and therefore, the position of the optic axis P which is the center of the ellipse is first calculated in the processor 5, and then the shape of the cornea is calculated.

Figure 6:
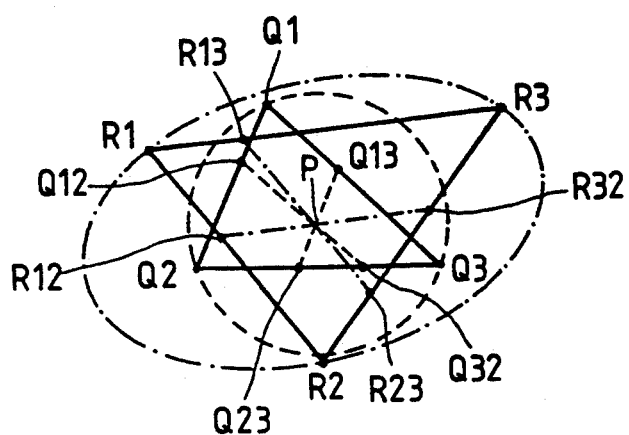
FIG. 6 illustrates a method of calculating the shape of a cornea according to the third embodiment.

A method of calculating the position of the optic axis P will now be described. FIG. 6 is an illustration in which the positions of the light sources 7a-7c, the reflected images 7A - 7C and the optic axis P are projected onto the same plane perpendicular to the optic axis P, and the positions of the light sources 7a-7c, the reflected images 4A - 4C and the optic axis P are designated by points Q1, Q2, Q3, R1, R2, R3 and P, respectively. First, the points of intersection between a straight line passing through the point P and drawn parallel to a segment Q1Q2 and segments Q2Q3 and Q3Q1 are defined as a point Q23 and Q13, and the points of intersection between a straight line passing through the point P and drawn parallel to a segment Q1Q3 and segments Q1Q2 and Q2Q3 are defined as a point Q12 and a point Q32. Assuming that the reflected image points at which the points Q12, Q23, Q32 And Q13 are to be reflected by the cornea Ec are points R12, R23, R32 and R13, a triangle Q1Q2Q3 is similar to a triangle Q12Q2Q32 and a triangle Q13Q23Q3 and therefore, a triangle R1R2R3 becomes similar to a triangle R12R2R32 and a triangle R13R23R3. So, the positions of image points R12 and R13 can be calculated from the following equations:

Length Q1Q12/length Q12Q2 = length R1R12/length R12R2

Length Q1Q13/length Q13Q3 = length R1R13/length R13R3

If two straight lines passing through the calculated points R12 and R13 and parallel to segments R1R3 and R1R12 are drawn, the point of intersection therebetween coincides with the position of the optic axis P. During the actual measurement of the shape of the cornea, the ratios of the above-mentioned equations may be calculated in advance from the positions of the light sources 7a-7c and the optic axis P, and the position of the optic axis P may be calculated from the reflected images 7A - 7C observed on the image sensor 3.

Figure 7:
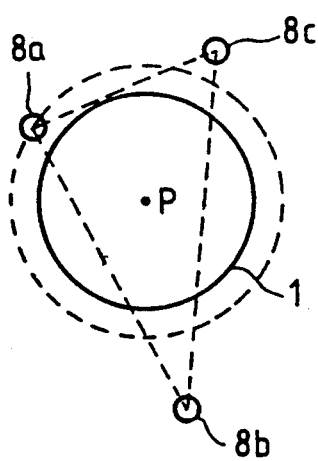
FIG. 7 shows the arrangement of measuring light sources according to a fourth embodiment.
Figure 8:
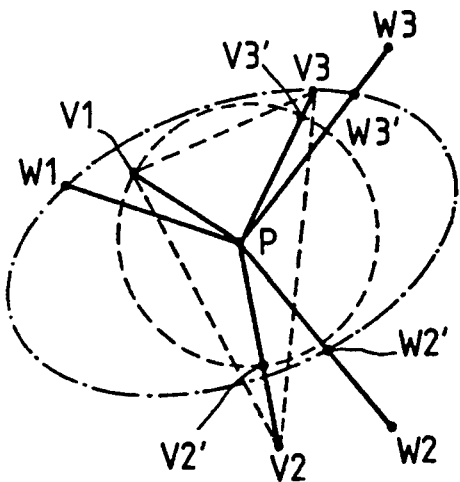
FIG. 8 illustrates a method of calculating the shape of a cornea according to the fourth embodiment.

FIG. 7 shows a fourth embodiment. In this embodiment, the construction of the apparatus is substantially similar to that of the first embodiment, and three light sources 8a-8c for the measurement of the shape of the cornea are provided at any positions on a plane perpendicular to the optic axis P near the objective lens 1. As in the first embodiment, light beams emitted from these light sources 8a-8c project three reflected images 7A - 7C onto the image sensor 3. In this embodiment, however, the light sources 8a-8c are not provided on the circumference of the same circle and therefore, if the shape of the cornea is directly calculated from the positions of the reflected images 7A - 7C, the value of the shape of the cornea will contain therein the influence of the fact that the positions of the light sources 8a-8c are not on the circumference of the same circle. So, as in the third embodiment, the position of the optic axis P is first calculated, and then a correction using the positions of the light sources 8a-8c and the optic axis P is effected for the reflected images 7A - 7C, and the positions of the reflected images 7A' - 7C' when the light sources 8a-8c are provided on the circumference of the same circle are calculated, whereafter the calculation of the shape of the cornea is effected on the basis Of an ellipse linking the reflected images 7A' - 7C' with the optic axis P as the center.

Describing the method of correction for the reflected images 7A - 7C, the positions of the light sources 8a-8c, the reflected images 7A - 7C and the optic axis P are designated by points V1, V2, V3, W1, W2, W3 and P, respectively. One of segments PV1, PV2 and PV3 which is smallest in length is first chosen. Assuming that the segment PV1 is smallest in length, points V2' and V3' are chosen on the segments PV2 and PV3, respectively, so as to satisfy the following equations:

Length PV 1 = length PV2'
Length PV1 = length PV3'

The points V1, V2' and V3' are on the circumference of the same circle about the point P and therefore, if two points W2' and W3' which satisfy the following equations are chosen on segments PW2 and PW3, respectively, points W1, W2' and W3' will be the positions of the corrected reflected images 8A' - 8C':

PV2/PV2' = PW2/PW2'
PV3/PV3' = PQ3/PQ3'

During the actual measurement of the shape of the cornea, the values of the ratios of the above-mentioned equations for effecting correction are calculated in advance from the positions of the light sources 8a-8c, and the shape of the cornea is calculated from the positions of the reflected images 8A' - 8C' subjected to the correction of the positions of the reflected images 7A - 7C observed on the image sensor 3.

In this case, even if the optic axis P exists on a segment linking two light sources, e.g. on a segment V1V2, there will be no hindrance to the above-described correction and the calculation of the shape of the cornea, but as already described with respect to the prior art, it is desirable that if possible, the optic axis P does not exist on the segment linking two light sources.

I claim:

1. A keratometer comprising:
   projection means for projecting more than three point sources of light onto the cornea of an eye to be examined;
   light receiving means for receiving more than three cornea-reflected images of the point sources of light projected by said projection means by a light position detector;
   means for detecting the centers of ellipses, each of the centers being detected on the basis of the position information of all images in a set of three cornea-reflected images selected from the more than three cornea-reflected images detected by said light position detector, said sets each for detecting each of the centers not being equal to each other;
   means for calculating elliptical shapes on the basis of the cornea-reflected images when said point sources of light exist on the circumference of he same circle and the centers of said ellipses; and
   means for detecting the information of the shape of the cornea of the eye to be examined from said elliptical shapes.

2. A keratometer according to claim 1, wherein said projection means projects six point sources of light on the circumference of the same circle, wherein two sets of three such point sources of light each are provided at each 120°, and wherein said projection means alternately turns on a first set and a second set of three such point sources of light.

3. A keratometer comprising:
   projection means for projecting three point sources of light onto the cornea of an eye to be examined;
   light receiving means for receiving the cornea-reflected images of the point sources of light projected by said projection means by a light position detector;
   means for detecting the center of an ellipse on the basis of the position information of all the three cornea-reflected images detected by said light position detector;
   means for calculating an elliptical shape on the basis of the cornea-reflected images when said point sources of light exist on the circumference of the same circle and the center of said ellipse; and
   means for determining the shape of the cornea of the eye to be examined from said elliptical shape, wherein said three point sources of light are disposed at equal intervals of 120° on the circumference of the same circle.

4. A keratometer according to claim 3, wherein said calculating means specifies the position of the center of gravity of a triangle linking the positions of the three cornea-reflected images detected by said light position detector as the center of the ellipse.

5. A keratometer comprising:
   projection means for projecting at least three point sources of light onto the cornea of an eye to be examined;
   light receiving means for receiving the cornea-reflected images of the point sources of light projected by said projection means by a light position detector; and
   means for detecting the center of an ellipse on the basis of the position information of all the three cornea-reflected images detected by said light position detector;
   means for calculating an elliptical shape on the basis of the center of the ellipse and the cornea-reflected images when said point sources of light exist on the circumference of the same circle; and
   means for determining the shape of the cornea of the eye to be examined from said elliptical shape, wherein said at least three point sources of light are on the circumference of the same circle and are disposed at unequal intervals.

6. A keratometer according to claim 5, wherein said calculating means extracts two triangles of a predetermined similarity ratio from a triangle linking the positions of the three cornea-reflected images detected by said light position detector and specifies the point of intersection between said two triangles as the center of the ellipse.

7. A keratometer comprising:
   projection means for projecting at least three point sources of light onto the cornea of an eye to be examined;
   light receiving means for receiving the cornea-reflected images of the point sources of light projected by said projection means by a light position detector; and
   means for detecting the center of an ellipse on the basis of the position information of all images in a set of three cornea-reflected images detected by said light position detector;
   means for calculating an elliptical shape on the basis of the cornea-reflected images when said point sources of light exist on the circumference of the same circle and the center of said ellipse; and means for determining the shape of the cornea of the eye to be examined from said elliptical shape, wherein said at least three point sources of light are not on the circumference of the same circle, the center of which is on an optical axis of said light receiving means, and are disposed at unequal intervals.

8. A keratometer according to claim 7, wherein said calculating means extracts two triangles of a predetermined similarity ratio from a triangle linking the positions of the three cornea-reflected images detected by said light position detector and specifies the point of intersection between said two triangles as the center of the ellipse.

9. A keratometer according to claim 8, wherein said calculating means extracts a cornea-reflected image for which the distances from said center of the ellipse to the positions of said cornea-reflected images are smallest, and wherein with the distance between the point source of light forming said cornea-reflected image and said center of the ellipse as the reference, said calculating means determines the ratio of the distances between the point sources of light forming the other cornea-reflected images and said center of the ellipse, and corrects the position of said cornea-reflected images on the basis of said ratio to thereby calculate the elliptical shape.

10. A keratometer comprising:
projection means for projecting at least three point sources of light onto the cornea of an eye to be examined;
light receiving means for receiving the cornea-reflected images of the point sources of light projected by said projection means by a light position detector;
means for detecting the center of an ellipse on the basis of the position information of all the three cornea-reflected images detected by said light position detector;
means for calculating an elliptical shape on the basis of the cornea-reflected imgaes when said point sources of light exist on the circumference of the same circle and the center of said ellipse, wherein said calculating means extracts two triangles of a predetermined similarity ratio from a triangle linking the positions of the three cornea-reflected images detected by said light position detector and specifies the point of intersection between said two triangles as the center of the ellipse; and
means for determining the shape of the cornea of the eye to be examined from said elliptical shape, wherein said at least three point sources of light are not on the circumference of the same circle and are disposed at unequal intervals.

11. A keratometer according to claim 10, wherein said calculating means extracts a cornea-reflected image for which the distances from said center of the ellipse to the positions of said cornea-reflected images are smallest, and wherein with the distance between the point source of light forming said cornea-reflected image and said center of the ellipse as the reference, said calculating means determines the ratio o the distances between the point sources of light forming the other cornea-reflected images and said center of the ellipse, and corrects the positions of said cornea-reflected images on the basis of said ratio to thereby calculate the elliptical shape.

* * * * *

UNITED STATES PATENT AND TRADEMARK OFFICE
CERTIFICATE OF CORRECTION

PATENT NO. : 5,325,134
DATED : June 28, 1994
INVENTOR(S) : YOSHIMI KOHAYAKAWA

It is certified that error appears in the above-indentified patent and that said Letters Patent is hereby corrected as shown below:

<u>COLUMN 4</u>:

Line 68, "Of" should read --of--.

<u>COLUMN 5</u>:

Line 55, "he" should read --the--.

<u>COLUMN 7</u>:

Line 26, "position" should read --positions--.

<u>COLUMN 8</u>:

Line 29, "o" should read --of--.

Signed and Sealed this

Eighth Day of November, 1994

Attest:

BRUCE LEHMAN

*Attesting Officer*  *Commissioner of Patents and Trademarks*